United States Patent [19]
Roth et al.

[11] Patent Number: 5,456,972
[45] Date of Patent: Oct. 10, 1995

[54] METHOD AND APPARATUS FOR GLOW DISCHARGE PLASMA TREATMENT OF POLYMER MATERIALS AT ATMOSPHERIC PRESSURE

[75] Inventors: John R. Roth; Peter P. Tsai, both of Knoxville, Tenn.

[73] Assignee: The University of Tennessee Research Corporation, Knoxville, Tenn.

[21] Appl. No.: 68,739

[22] Filed: May 28, 1993

[51] Int. Cl.⁶ .................................................. D03D 3/00
[52] U.S. Cl. .................. 428/224; 156/272.2; 156/272.6; 264/483; 428/903; 429/247; 429/249; 429/250
[58] Field of Search ................................... 429/247, 249, 429/250; 428/224, 903; 264/22; 156/272.2, 272.6

[56] References Cited

U.S. PATENT DOCUMENTS

| | | | |
|---|---|---|---|
| 5,227,172 | 7/1993 | Deeds | 264/22 |
| 5,270,137 | 12/1993 | Kubota | 429/249 |

OTHER PUBLICATIONS

Authors: Von Engel, A,; Seeliger, R.; and Steenbeck, M., Title: On The Glow Discharge At High Pressure. Publication: *Ziet, fur Physik*, vol. 85 (1993) pp. 144–160.

English language translation of above from original German.

EPO Publication No. 0,068,775 Issue Date: Jan. 5, 19083, Inventor: Hata, et al.

EPO Publication No. 0,117,561, Issue Date: Sep. 5, 1984, Inventor Akagi, et al.

Authors: Wakida, T.; Kawamura, H.; Han, L.; Hwan Kim, K.; Goto, T.; and Takagishi, T., Title: Changes In Surfaace Properties of Poly(Ethylene Terephthalate) Treated With Low Temperature Plasma: Effect of Pretreatment With Dimethylformamide, Publication: *Sen–I Gakkaishi*, vol. 42 No. 2 (1986).

Authors: Wakida, T.; Kawamura, H.; Song, J. C.; Goto, T.; Takagushi, T., Title: Surface Free Energy Of Poly(Ethylene Terepathalate) And Nylon 6 Films Treated With Low Temperature Plasma, Publication: *Sen–I Gakkaishi*, vol. 43, No., 7 (1987).

Japanese Patent No. 62–235,339, Issue Date: Oct. 15, 1987, Inventors: M. Kogoma, et al.

Author: Rakowski, W. Title: Plasma Modification Of Wool Under Industrial Conditions, Publication: *Melliand Textilberichte*, vol. 70 (1989) pp. 780–785.

Authors: Reitz, H.; Schwarz, R.; Salge, J. G. H., Title Power Modulation For Dielectric Barrier–Discharges, Publication: Paper presented at *Twentieth Power Modulator Symposium*, 1992.

Authors: Roth, J. R.; Spence, P. D.; Liu C., Title: Plasma–Related Characteristics Of A Steady–State Glow Discharge At Atmospheric Pressure, Publication: Paper 2P–18, *Proc. 1993 IEEE International Converence on Plasma Science*, Vancouver, B.C. IEEE Catalog No. 93–CH3334–0, ISBN 0–7803–1360–7 (1993), p. 129.

Authors: Roth, J.R,; Spence, P. D.; Liu, C., Title: Preliminary Measurements Of The Plasma Properties Of A One Atmosphere Glow Discharge Plasma. Publication: Paper presented at *35th Annual Meeting of the APS Division of Plasma Physics*, St. Louis, MO., Nov. 1–5, 1993;. APS Bulletin, Series II, vol. 38, No. 10 (1992), p. 1901.

(List continued on next page.)

*Primary Examiner*—James J. Bell
*Attorney, Agent, or Firm*—Weiser & Associates

[57] ABSTRACT

Polymer materials such as film and fabrics, woven, nonwoven and meltblown, may be non-destructively surface treated to improve water wettability by exposure to a glow discharge plasma sustained at substantially atmospheric pressure in a modified gas atmosphere comprising helium or argon.

29 Claims, 5 Drawing Sheets

OTHER PUBLICATIONS

Author: Noiki Kanda, Mashuhiro Kogoma, Hiroshi Hinno, Hiroshi Uchiyama and Sachiko Okazaki, Title: Atmospheric Pressure Glows Plasama and Its Application to Surface Treatment and Film Disposition, Publication; International Union of Pure and Applied Chemistry. 10th International Symposium on Plasma Chemistry. Symposium Proceedings, vol. 3, Bochum, Germany, Aug. 4–9, 1991.

Authors: M. Kogoma, H. Kasai, K. Takahashi, T. Moriwaki and S. Okazaki, Title: Wettability Control of a Plastic Surface by $CF_4$–$O_2$ Plasma and Its Etching Effect, Publication: J. Phys. D: Appl. Phys., vol. 20, (1987).

Authors: S. Kanazawa, M. Kogoma, T. Moriwaki and S. Okazaki, Title: Stable Glow Plasma at Atmospheric Pressure, Publication: J. Phys. D: Appl. Phys., vol. 21 (1988).

Author: Chaoyo Liu, Title: Plasma–Related Characteristics of a Steady–State Glow Discharge at Atmospheric Pressure, Publication: Presented at the 1993 Sigma XI Graduate Student Paper Competition, The University of Tennessee, Knoxville. Tenn. Mar. 4, 1993.

Authors: C. Liu and J. R. Roth, Title: Characteristics of a Steady–State, Low Power Glow Discharge at Atmospheric Pressure, Publication: Bulletin of the American Physical Society Series II, vol, 37, No. 6, Nov. 1992.

Authors: J. Reece Roth, Mounir Laroussi and Chaoyo Liu, Title: Experimental Generation of a Steady–State Glow Discharge at Atmospheric Pressure, Publication: 1992 19th IEEE International Conference on Plasma Science, Conference Record –Abstracts –1–3 Jun. 1992.

Author: Witold Rakowski, Title: Effect and Cost of Plasma Treatment of Polyporpylene Melt Blown Webs, Publication: Second Annual TANDEC Conference. 13–16 Oct. 1992.

METHOD AND APPARATUS FOR GLOW DISCHARGE PLASMA TREATMENT OF POLYMER MATERIALS AT ATMOSPHERIC PRESSURE

LICENSE RIGHTS

This invention was made with government support under Contract No. AFOSR-89-0319 awarded by the U.S. Air Force. The government has certain rights in this invention.

BACKGROUND OF THE INVENTION

1. Field of Invention

The present invention relates to a method and apparatus for modifying the surface properties of organic and inorganic polymer materials such as film and fabric, woven and non-woven.

2. Description of the Prior Art

One of the many utilities for meltblown polymer web is as a wet cell battery plate separator. The base polymer compound is impervious to the electrolyte. The meltblown, non-woven fabric structure is ion permeable if the surface thereof is thoroughly wetted by the electrolyte. Unfortunately, this latter requirement of wettability is not an inherent characteristic of most commercial polymers such as nylon, polypropylene, polyethylene and poly(ethylene terephthalate).

Although meltblown webs of these polymers are currently used as battery plate separators, wettability is achieved chemically by means of surfactants. This process not only generates hazardous industrial waste but produces a product of limited utility life.

Wettability is also a desirable property for tissue and cloth used to wipe or clean the body, for surgical sponges, wound dressings, feminine hygiene products and reuseable woven knit fabrics. Similarly, wettability is an important material surface property for printing and laminating.

Some success has been recently achieved by a glow discharge plasma treatment of meltblown polymer webs. The term "plasma" usually describes a partially ionized gas composed of ions, electrons and neutral species. This state of matter may be produced by the action of either very high temperatures, or strong direct current (DC) or radio frequency (RF) electric fields. High temperature or "hot" plasmas are represented by celestial light bodies, nuclear explosions and electric arcs. Glow discharge plasmas are produced by free electrons which are energized by an imposed DC or RF electric field and then collide with neutral molecules. These neutral molecule collisions transfer energy to the molecules and form a variety of active species including metastables, individual atoms, free radicals and ions. These active species are chemically active and/or capable of physically modifying the surface and may therefore serve as the basis of new chemical compounds and property modifications of existing compounds.

Low power plasmas known as dark discharge coronas have been widely used in the surface treatment of thermally sensitive materials such as paper, wool and synthetic polymers such as polyethylene, polypropylene, polyolefin, nylon and poly(ethylene terephthalate). Because of their relatively low energy content, corona discharge plasmas can alter the properties of a material surface without damaging the surface.

Glow discharge plasmas represent another type of low power density plasma useful for non-destructive material surface modification. These glow discharge plasmas can produce useful amounts of strong ultraviolet radiation. Glow discharge plasmas have the additional advantage therefore of producing UV radiation in the simultaneous presence of active species. However, glow discharge plasmas have heretofore been successfully generated typically in low pressure or partial vacuum environments below 10 torr. Several polymer species of meltblown webs exposed to low pressure glow discharge plasmas respond with enhanced surface wettability characteristics. However, the chemical/physical mechanism is not understood and the characteristic is lost upon drying. Rewettability remains elusive.

It is an object of the present invention, therefore, to provide a non-byproduct producing process for enhancing the wettability of meltblown polymer webs and any type of polymeric substrate.

Another object of the invention is to teach a glow discharge plasma process for treating meltblown polymer web that provides a stable, rewettable product.

Another object of the invention is to provide a method and apparatus for continuously processing a meltblown polymer web of indefinite length through a glow discharge plasma at atmospheric pressure and standard temperature.

It is, therefore, an object of the present invention to teach the construction and operating parameters of a glow discharge plasma having operability in an environmental pressure of about one atmosphere or slightly greater.

INVENTION SUMMARY

These and other objects of the invention to be subsequently explained or made apparent are accomplished with an apparatus based upon a pair of electrically insulated metallic plate electrodes. These plates are mounted in face-to-face parallel alignment with means for reciprocatory position adjustment up to about 5 cm of separation. Preferably, the plates are water cooled and coated with a dielectric insulation.

A radio frequency power amplifier connected to both plates delivers at least 180 watts of power at a working voltage of 1 to at least 5 KV rms and at 1 to 100 KHz.

At least in the volume between the plates wherein the plasma field is established, a one atmosphere charge of helium or argon is established and maintained for processing material such as polymer film and web to produce desired surface characteristics such as wettability and re-wettability.

BRIEF DESCRIPTION OF THE DRAWINGS

Relative to the drawings wherein like reference characters designate like or similar elements throughout the several figures of the drawings.

DESCRIPTION OF THE PREFERRED EMBODIMENT

Figure 1:
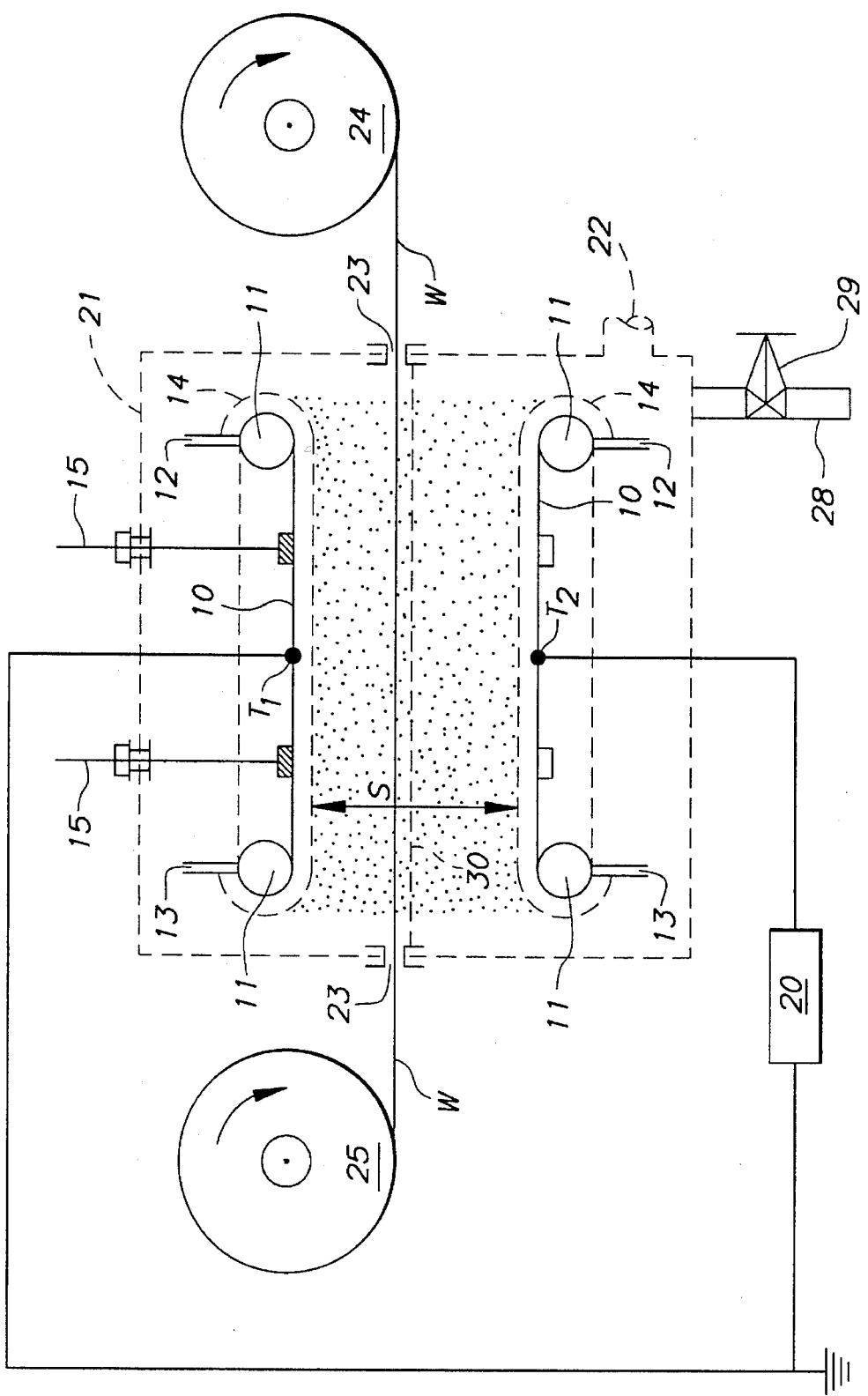
FIG. 1 is a schematic of the present invention component assembly.

Referring to the invention schematic illustrated by FIG. 1, the electrodes 10 are fabricated of copper plate having a representative square plan dimension of 25 cm×25 cm. Silver soldered to the plates 10 are closed loops 11 of 1.9 cm copper tubing having hose nipples 12 and 13 connected therewith on opposite sides of the closed tubing loop. Not shown are fluid flow conduits connected to the inlet nipples 12 for delivering coolant fluid to the loop 11 and to the outlet nipples 13 for recovering such coolant fluid.

The integral metallic units comprising plates 10 and tubing 11 are covered with a high dielectric insulation material 14.

Preferably, some mechanism should be provided for adjusting the distance d between plates 10 up to about 5 cm separation while maintaining relative parallelism. Such a mechanism is represented schematically in FIG. 1 by the rod adjusters 15 secured to the upper plate 10. This arrangement anticipates a positionally fixed lower plate 10.

Energizing the plates 10 is a low impedance, high voltage, R.F. power amplifier 20 having independently variable voltage and frequency capacities over the respective ranges of 1 to at least 5 KV and 1 to 100 KHz.

Surrounding the plate assembly is an environmental isolation barrier 21 such as a structural enclosure suitable for maintaining a controlled gas atmosphere in the projected plan volume between the plates 10. Inlet port 22 is provided to receive an appropriate gas such as helium or argon, mixtures of either with air or a mixture of argon with helium. In any case, gas pressure within the isolation barrier 21 is substantially ambient thereby obviating or reducing the need for gas tight seals. Normally, it is sufficient to maintain a low flow rate of the modified atmosphere gas through the inlet port 22 that is sufficient to equal the leakage rate. Since the pressure within the isolation barrier 21 is essentially the same as that outside the barrier, no great pressure differential drives the leakage rate. A vent conduit 28 controlled by valve 29 is provided as an air escape channel during initial flushing of the enclosure. Thereafter, the valve 29 is closed for normal operation.

Narrow material flow slits 23 are provided in the isolation barrier 21 to accommodate passage of a material web W between the plates 10 as drawn from a supply reel 24 onto a rewind reel 25. Drive for the reels 24 and 25 is controlled to provide a predetermined residence time between the plates 10 and within the plasma for any given web element.

Figure 7:
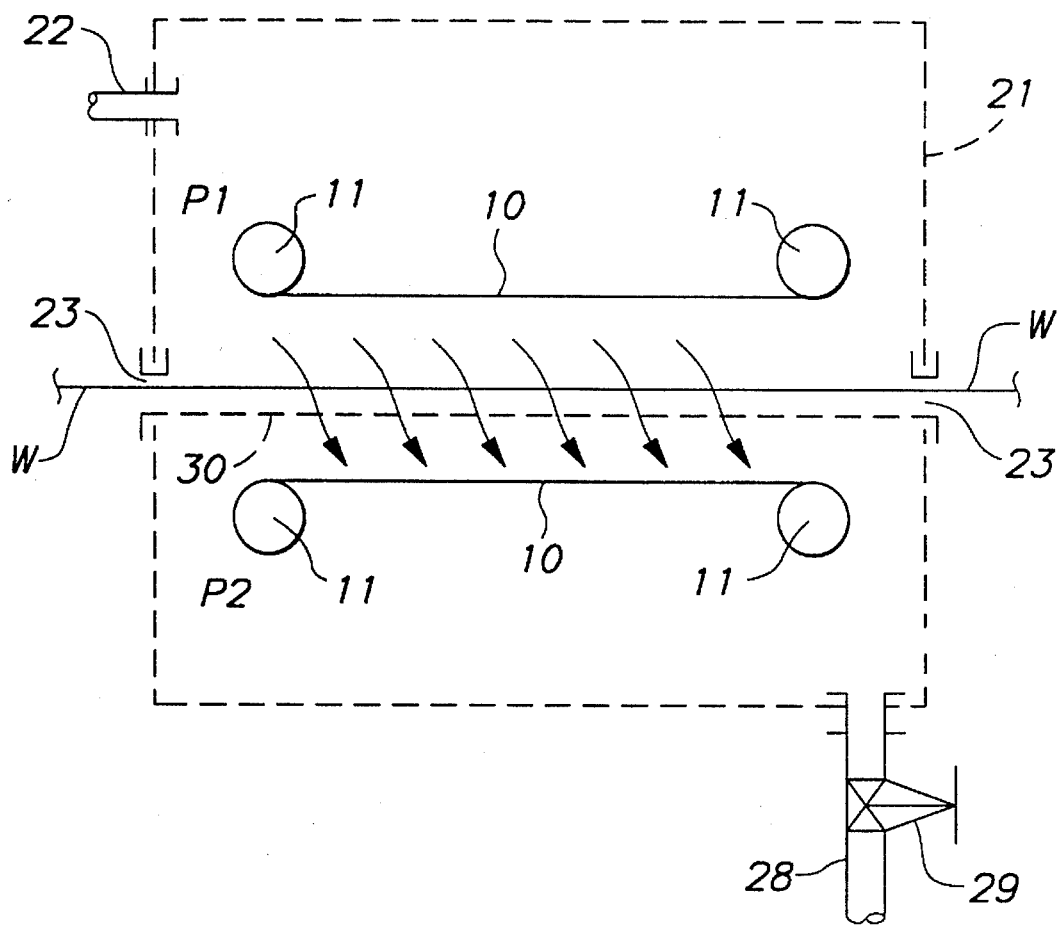
FIG. 7 represents an alternative embodiment of the invention.

The FIG. 7 embodiment of the invention provides an electrically grounded screen 30 to support the web W as it is drawn between the opposite material flow slits 23. This configuration attenuates an accumulated electrical charge on the web and also structurally supports the traveling web as a pressure differential membrane between an upper, gas inlet chamber and a lower, vent chamber. This swept flow differential assures an internal saturation of the web W by the gas supported plasma.

EXAMPLE 1

Figure 2:
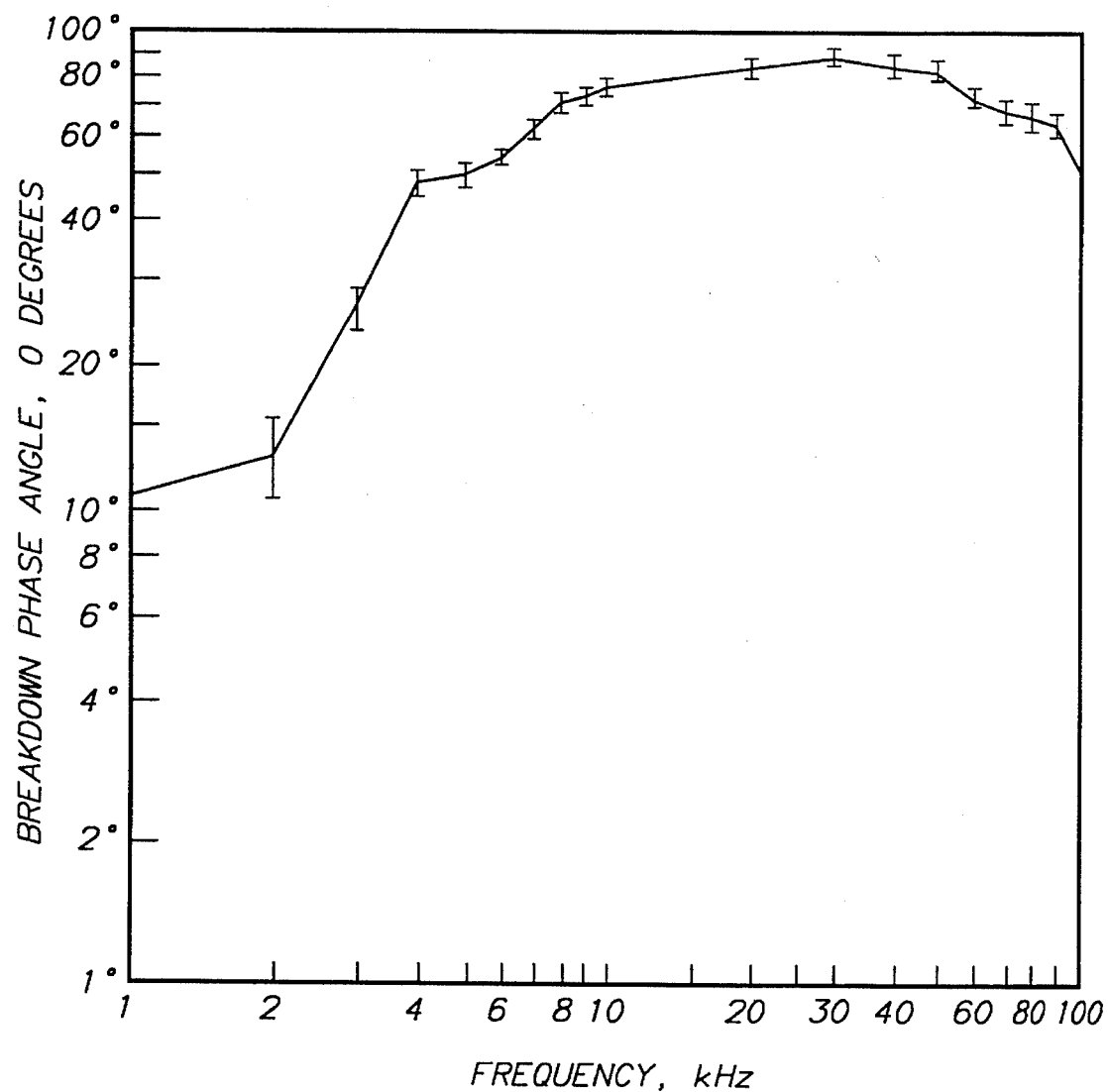
FIG. 2 is a graph of amplifier frequency and corresponding breakdown current phase angles respective to a particular operating example of the invention.
Figure 3:
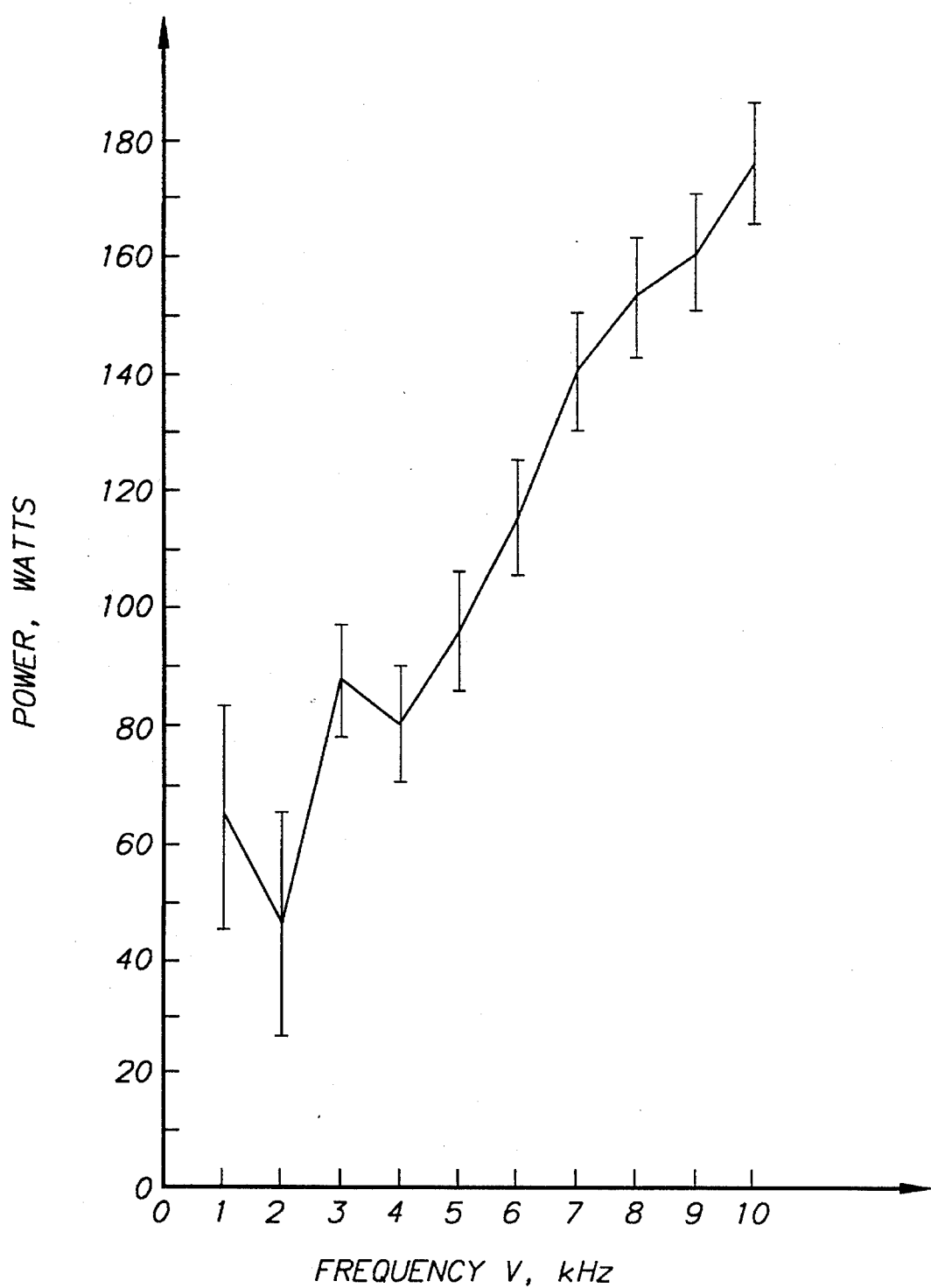
FIG. 3 is a graph of amplifier frequency and corresponding power consumption respective to a particular operating example of the invention.

In a first operational example of the invention, the FIG. 1 described physical apparatus sustained a glow discharge plasma in one atmosphere of helium at standard temperature with a separation distance d of 3.0 cm between plates 10. The plates were energized with a 4.4 KV rms working potential. Holding these parameters constant, R.F. frequency was increased as an independent variable. As the dependent variable, FIG. 2 charts the corresponding breakdown current phase angle. Similarly, FIG. 3 charts the power required to sustain the plasma at the respective R.F. frequencies.

EXAMPLE 2

In a second operational example of the invention, the FIG. 1 described physical apparatus is used to sustain a glow discharge plasma in one atmosphere of helium at standard temperature with a separation distance d of 1.0 cm between plates 10. In this example, the energy frequency was held constant at 30 KHz while plate potential was manipulated as the independent variable and current breakdown phase angle, θ, (Table 1) and power, W, (Table 2) measured as dependent variables.

TABLE 1

| V(KV) | 1 | 1.5 | 2 | 2.5 | 3 | 3.5 |
|---|---|---|---|---|---|---|
| Θ(deg) | 28 | 40 | 61 | 46 | 65 | 76.5 |

TABLE 2

| V(KV) | 1 | 1.5 | 2 | 2.5 | 3 | 3.5 |
|---|---|---|---|---|---|---|
| P(W) | 7 | 13 | 22 | 57 | 50 | 44.9 |

EXAMPLE 3

A third operational example of the invention included a one atmosphere environment of helium between a 1 cm separation distance d between plate electrodes 10 charged at 1.5 KV rms potential. The R.F. frequency was manipulated as the independent variable. As a measured dependent variable, Table 3 reports the corresponding phase angle θ of breakdown current. The measured dependent variable of Table 4 reports the corresponding power consumption data.

TABLE 3

| f(KHz) | 10 | 20 | 30 | 40 | 50 | 60 | 70 | 80 | 90 | 100 |
|---|---|---|---|---|---|---|---|---|---|---|
| Θ(deg) | 43 | 32 | 43 | 52 | 54 | 61 | 60 | 56 | 45 | 22.5 |

TABLE 4

| f(KHz) | 10 | 20 | 30 | 40 | 50 | 60 | 70 | 80 | 90 | 100 |
|---|---|---|---|---|---|---|---|---|---|---|
| P(W) | 5 | 8 | 11 | 19 | 35 | 43 | 47 | 57 | 89 | 124 |

EXAMPLE 4

The largest volume helium plasma of 2.8 liters was achieved with the above described apparatus at a 4.5 cm plate separation having a 5 KV rms potential charged at 4 KHz.

Meltblown webs formed from nylon, poly(ethylene terephthalate), polypropylene and polyethylene have been processed by exposure to the glow discharge plasma described herein to produce desired material characteristics, increased wettability and re-wettability.

Wettability of a material is objectively measured by either or both of two tests including (a) the angle of a water bead supported on the material surface and (b) the time required to wick along a predetermined material length.

By such tests, it was determined that polypropylene, polyester and polyethylene film experienced a significant wettability and re-wettability improvement after a 2.5 minute plasma exposure as evidenced by a greatly reduced bead angle.

A poly(ethylene terephthalate) web, after 2.5 minutes of glow discharge plasma exposure to a 5 KV, 4 KHz across a 4.5 cm plate separation, experienced a 0° surface bead angle and a 37.37 second wicking rate determined by the INDA standard absorption test. Prior to plasma exposure, the web had a large surface bead angle and no wicking capacity.

Similarly, after only 60 seconds of exposure to the same plasma, a nylon web, having a high surface bead angle and no wicking capacity enjoyed a 0° surface bead angle and a 16.61 second wicking rate (INDA standard test) upon wetting or re-wetting.

It will be understood by those of ordinary skill in the art that the present invention is capable of numerous arrangements, modifications and substitutions of parts without departing from the scope of the invention.

Figure 4:
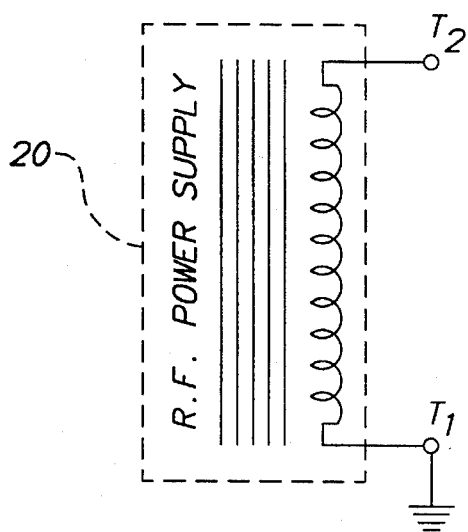
FIGS. 4, 5 and 6 represent alternative power supply circuits.
Figure 5:
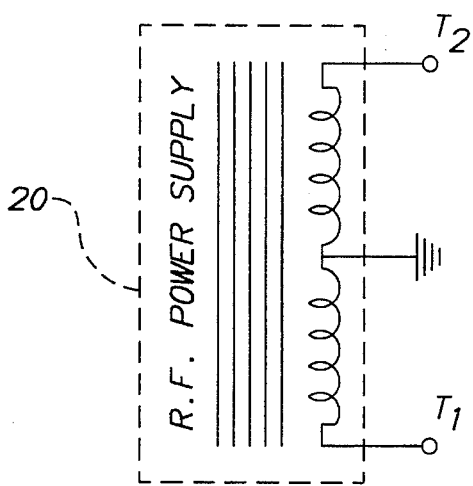
Figure 6:
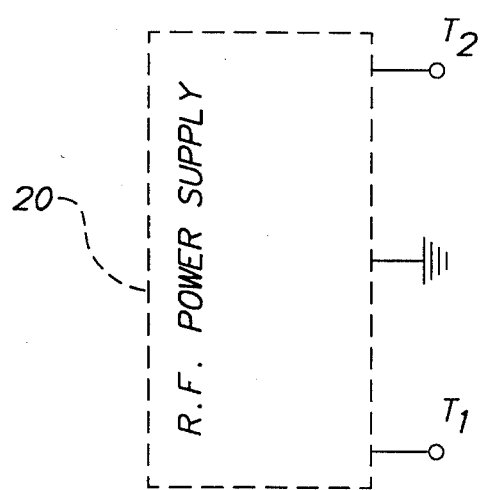

In particular, FIGS. 4 through 6 represent respective power supply options having respective attractions. FIG. 4 corresponds to the FIG. 1 illustration wherein the top electrode terminal $T_1$ is connected to ground potential and the bottom terminal $T_2$ is charged at the full working potential.

FIGS. 5 and 6 are electrical equivalents wherein the $T_1$ and $T_2$ voltages are 180° out of phase but at only half the maximum potential. FIG. 5 represents a grounded center tap transformer whereas FIG. 6 represents a solid state power circuit embodiment. As our invention, however,

We claim:

1. A method for improving the wettability of a meltblown polymer web or film, comprising the steps of generating a sustained atmospheric pressure of about one atmosphere, glow discharge plasma between a pair of spaced plate electrodes, wherein said electrodes are energized over a range of about 1 to at least 5 KV rms at a radio frequency of about 1 to 100 KHz, and drawing said web or film in the space between said electrodes and within said glow discharge plasma for a predetermined period of time.

2. A method as described by claim 1 wherein a volume defined by the space between said electrodes is charged with a noble gas.

3. A method as described by claim 2 wherein said gas is helium.

4. A method as described by claim 2 wherein said gas is a mixture of helium and air.

5. A method as described by claim 2 wherein said gas is argon.

6. A method as described by claim 2 wherein said gas is a mixture of argon and air.

7. A method as described by claim 2 wherein said gas is a mixture of argon and helium.

8. A method as described by claim 1 wherein said web is of indefinite length drawn between said electrodes at a substantially continuous rate to provide a predetermined elapsed residence time within said plasma.

9. The method of claim 1 wherein said glow plasma discharge includes ultraviolet radiation in the simultaneous presence of active species.

10. The method of claim 1 wherein prior to the step of exposing the web or film between the spaced electrode plates, the web formed from the polymeric material.

11. The method of claim 1 wherein said electrodes are energized by a radio frequency power amplifier of at least 5 watts.

12. The method of claim 1 wherein the space between the electrode plates is charged with a noble gas.

13. The method of claim 12 wherein the gas is a mixture of helium and air or argon and air.

14. A meltblown polymer web or film having a surface of enhanced wettability and re-wettability produced by a predetermined period of exposure of said web or film to a sustained, atmospheric pressure of about one atmosphere, glow discharge plasma generated by about 1 to at least 5 KV rms potential at a radio frequency of about 1 to 100 KHz.

15. A meltblown polymer web as described by claim 14 wherein said plasma is sustained by a noble gas.

16. A meltblown polymer web as described by claim 15 wherein said gas is helium.

17. A meltblown polymer web as described by claim 15 wherein said gas is a mixture of helium and air.

18. A meltblown polymer web as described by claim 15 wherein said gas is argon.

19. A meltblown polymer web as described by claim 15 wherein said gas is a mixture of argon and air.

20. A meltblown polymer web as described by claim 15 wherein said gas is a mixture of argon and helium.

21. A meltblown polymer web as described by claim 14 formed from polypropylene.

22. A meltblown polymer web as described by claim 14 formed from nylon.

23. A meltblown polymer web as described by claim 14 formed from polyethylene.

24. A meltblown polymer web as described by claim 14 formed from polyolefin.

25. A meltblown polymer web as described by claim 14 from poly(ethylene terephthalate).

26. The meltblown polymer web as described by claim 14 which is a polyester polymer.

27. The meltblown polymer web of claim 14 wherein the web or film is selected from the group consisting of polypropylene, polyester and polyethylene and nylon.

28. The meltblown polymer of claim 27 wherein the web is a nonwoven web.

29. The meltblown polymer web of claim 28 wherein said plasma includes ultraviolet radiation in the simultaneous presence of active species.

* * * * *

UNITED STATES PATENT AND TRADEMARK OFFICE
CERTIFICATE OF CORRECTION

PATENT NO. : 5,456,972
DATED : October 10, 1995
INVENTOR(S) : Roth et al.

It is certified that error appears in the above-indentified patent and that said Letters Patent is hereby corrected as shown below:

On title page, item [75]

Inventors, delete "John R. Roth; Peter P. Tsai, both of Knoxville, Tenn." and replace with --- John R. Roth; Peter P. Tsai; Larry C. Wadsworth; Chaoyu Liu; all of Knoxville, Tenn. ---

Signed and Sealed this

Nineteenth Day of March, 1996

Attest:

BRUCE LEHMAN

Attesting Officer     Commissioner of Patents and Trademarks